US007629458B2

(12) United States Patent
Niddam-Hildesheim et al.

(10) Patent No.: US 7,629,458 B2
(45) Date of Patent: *Dec. 8, 2009

(54) PREPARATION OF LEVOFLOXACIN AND HEMIHYDRATE THEREOF

(75) Inventors: Valerie Niddam-Hildesheim, Even-Yeouda (IL); Neomi Gershon, Rosh Ha-Ain (IL); Ehud Amir, Tel Aviv (IL); Shlomit Wizel, Petah Tiqva (IL)

(73) Assignee: Teva Pharmaceutical Industries Ltd., Petish Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/263,192

(22) Filed: Oct. 3, 2002

(65) Prior Publication Data

US 2003/0130507 A1    Jul. 10, 2003

Related U.S. Application Data

(60) Provisional application No. 60/354,939, filed on Feb. 11, 2002, provisional application No. 60/334,316, filed on Nov. 29, 2001, provisional application No. 60/326,958, filed on Oct. 3, 2001.

(51) Int. Cl.
    *C07D 498/06* (2006.01)
(52) U.S. Cl. .......................... 544/101; 544/99
(58) Field of Classification Search ................. 544/101
    See application file for complete search history.

(56) References Cited

U.S. PATENT DOCUMENTS

| | | | |
|---|---|---|---|
| 4,382,892 | A | 5/1983 | Hayakawa et al. |
| 4,777,253 | A | 10/1988 | Mitscher et al. |
| 5,051,505 | A | 9/1991 | Park et al. |
| 5,053,407 | A | 10/1991 | Hayakawa et al. |
| 5,142,046 | A | 8/1992 | Hayakawa et al. |
| 5,155,223 | A | 10/1992 | Preiss |
| 5,237,060 | A | 8/1993 | Schriewer et al. |
| 5,521,310 | A | 5/1996 | Carretero Gonzalvez et al. |
| 5,539,110 | A | 7/1996 | Kim et al. |
| 5,545,737 | A | 8/1996 | Sato et al. |
| 6,229,017 | B1 | 5/2001 | Lui et al. |
| 6,316,618 | B1 | 11/2001 | Park et al. |
| 6,872,823 | B1 | 3/2005 | Sato et al. |
| 7,425,628 | B2 | 9/2008 | Niddam-Hildesheim et al. |
| 2003/0130507 | A1 | 7/2003 | Niddam-Hildesheim et al. |
| 2004/0152701 | A1 | 8/2004 | Reddy et al. |
| 2005/0124629 | A1 | 6/2005 | Niddam-Hildesheim et al. |
| 2005/0222409 | A1 | 10/2005 | Niddam-Hildesheim et al. |
| 2006/0276463 | A1 | 12/2006 | Sharma et al. |
| 2008/0097095 | A1 | 4/2008 | Chava et al. |

FOREIGN PATENT DOCUMENTS

| | | |
|---|---|---|
| CA | 1167840 | 5/1984 |
| CA | 2044338 | 12/1991 |
| CA | 1304080 | 6/1992 |
| DE | 3543513 | 6/1987 |
| DE | 4019023 | 12/1991 |
| DE | 3687599 | 5/1993 |
| EP | 47005 | 3/1982 |
| EP | 206 283 | 12/1986 |
| EP | 225552 | 6/1987 |
| EP | 0 444 678 B1 | 9/1991 |
| EP | 0461501 | 12/1991 |
| EP | 619311 | 10/1994 |
| EP | 1073662 | 2/2001 |
| EP | 1 211 254 A | 6/2002 |
| EP | 1 451 194 | 9/2004 |
| EP | 1 460 997 | 9/2004 |
| EP | 1 772 457 | 4/2007 |
| EP | 1 992 629 | 11/2008 |
| ES | 2055656 | 8/1994 |
| IN | 719/MUM/2005 | 5/2005 |
| JP | 62-145088 | 6/1987 |
| JP | 62-198685 | 9/1987 |
| JP | 2-178287 | 7/1990 |
| JP | 4-234890 | 8/1992 |
| JP | 4-364185 | 12/1992 |
| JP | 6-49074 | 2/1994 |
| JP | 6032776 | 2/1994 |
| JP | 11-349589 | 12/1999 |
| JP | 2001-509476 | 7/2001 |
| WO | WO 00/50428 | 8/2000 |
| WO | WO 01/18005 A | 3/2001 |
| WO | WO 03/045329 | 6/2003 |
| WO | WO 2004/055025 | 7/2004 |
| WO | WO 2006/009374 | 1/2006 |
| WO | WO 2008/077643 | 7/2008 |

OTHER PUBLICATIONS

Joachim Ulrich, "Kirk-Othmer Encyclopedia of Chemical Technology", John Wiley & Sons, 2002.).*
West, Anthony R., Solid State Chemistry and its Applications, Wiley, New York, 1988, pp. 358 & 365.*
Riddick, John A. and Bunger, William B., "Organic Solvents", Wiley-Interscience, 1965, New York, p. 643.*

(Continued)

*Primary Examiner*—Kahsay T Habte
(74) *Attorney, Agent, or Firm*—Kenyon & Kenyon LLP (57) ABSTRACT

The invention provides a method for preparing levofloxacin hemihydrate, comprising:
    maintaining levofloxacin at a first elevated temperature in a first solvent;
    adding a polar solvent to precipitate the levofloxacin hemihydrate, wherein the polar solvent comprises water; and
    recovering the levofloxacin hemihydrate.

The invention also provides a method of converting a levofloxacin form to levofloxacin hemihydrate, comprising storing one or more forms selected from the group consisting of Forms A, B, C, F, G and H for a sufficient time to permit the one or more forms to convert to levofloxacin hemihydrate.

28 Claims, 10 Drawing Sheets

OTHER PUBLICATIONS

Hiroaki Kitaoka, "Effect of Dehydration on the Formation of Levofloxacin Pseudopolymorphs," Chem. Pharm. Bull., vol. 43, No. 4 (1995) pp. 649-653.

S. Arulla et al., "Pro-and Anti-oxidant Effects of Some Antileprotic Drugs in vitro and Their Influence on Super Oxide Dismutase Activity," Arzneim-Forsch./Drug Res., vol. 48 (II), No. 10 (1998) pp. 1024-1027.

Kang, Soon Bang, et al.; "An Improved Synthesis of Levofloxacin", Heterocycles, 45(1), 137-145, 1997, p. 137.

Opposition dated Jul. 4, 2007 filed by Ratiopharm GmbH in the related European Patent EP 1 451 194 B1.

Bohm et al., "Kristalle: Asthetisch nach außen, regelmaβig nach innen", Wirkstoffdesign, 239-240 (1996).

"Common Laboratory Techniques: Crystallization", Organic Laboratory Manual (1997) [retrieved from web: http://web.archive.org/web/19991003121551/http://www.umsl.edu/~orglab/].

Cross, "Fluoroquinolones", Seminars in Pediatric Infectious Diseases, 12(3):211-223 (2001).

Atarashi, Shohgo et al., "Synthesis and antibacterial activities of optically active ofloxacin and its fluoromethyl derivative", Chemical & Pharmaceutical Bulletin, 35(5): 1896-1902 (1987).

English translation of Japanese Office Action, dated Sep. 16, 2008, from related Japanese Patent Application No. 2007-216178.

Japanese Office Action, dated May 12, 2009, from corresponding Japanese Patent Application No. 2007-216178, and English translation thereof.

* cited by examiner

PREPARATION OF LEVOFLOXACIN AND HEMIHYDRATE THEREOF

CROSS-REFERENCE TO RELATED APPLICATIONS

This application claims the priority of provisional application Ser. Nos. 60/326,958, filed Oct. 3, 2001, 60/334,316, filed Nov. 29, 2001 and 60/354,939, filed Feb. 11, 2002. The entire content of each of these applications is incorporated herein by reference. The entire content of non-provisional application Ser. No. 10/262,965, filed Oct. 3, 2002, now abandoned, is also incorporated herein by reference.

FIELD OF THE INVENTION

The present invention relates to processes for preparing levofloxacin and novel forms thereof.

BACKGROUND OF THE INVENTION

Levofloxacin is a broad spectrum synthetic antibiotic. Levofloxacin is the S-enantiomer of the racemate, ofloxacin, a fluoroquinolone antimicrobial agent. The antibacterial activity of ofloxacin resides primarily in the S-enantiomer. The mechanism of action of levofloxacin and other fluoroquinolone antimicrobials involves the inhibition of DNA gyrase (bacterial topolsomerase II), an enzyme required for DNA replication, transcription repair and recombination. Levofloxacin is available as LEVAQUIN® which may be orally administered or administered intravenously.

Levofloxacin is a chiral fluorinated carboxyquinolone. Its chemical name is (S)-9-fluoro-2,3-dihydro-3-methyl-10-(4-methyl-1-piperazinyl)-7-oxo-7H-pyrido[1,2,3-de]-1,4-benzoxazine-6-carboxylic acid (CAS Registry No. 100986-85-4). The chemical structure of levofloxacin is shown as Formula I.

Formula I

U.S. Pat. No. 4,382,892 is directed toward pyrido[1,2,3-de][1,4]benzoxazine derivatives and methods of preparing them.

U.S. Pat. No. 5,053,407 is directed toward optically active pyridobenzoxazine derivatives, processes for preparing the same, and intermediates useful for preparing such derivatives.

U.S. Pat. No. 5,051,505 is directed toward processes for preparing piperazinyl quinolone derivatives. The process comprises reacting dihaloquinolones with piperazine derivatives and tetraalkyl ammonium halides in the presence of a polar solvent such as acetonitrile, dimethylformamide, pyridine, sulfolane and dimethyl sulfoxide.

U.S. Pat. No. 5,155,223 is directed toward the preparation of quinolinecarboxylic acids.

U.S. Pat. No. 5,545,737 discloses selectively producing a levofloxacin hemihydrate or monohydrate by controlling the water content of an aqueous solvent in which levofloxacin is dissolved during a crystallization.

Levofloxacin Forms

Three polymorphic forms (anhydrous α, β, γ) and two pseudopolymorphic forms (hemihydrate and monohydrate) of levofloxacin are mentioned in the literature. Hemihydrate and monohydrate forms are mentioned in EP 0444 678 B1 and in U.S. Pat. No. 5,545,737. These two patents are directed toward processes for the preparation of hemihydrate form free of monohydrate and for the preparation of monohydrate free of hemihydrate.

The article titled "Effect of dehydration on the formation of Levofloxacine Pseudopolymorphs," Chem. Pharm. Bull. 43(4) 649-653 (1995), examines the physical properties of the hydrates forms of levofloxacin. According to the article, heating the hemihydrate form resulted in a removal of the hydrated water to give anhydrous form γ. Further heating resulted in the formation of anhydrous form β, and then the formation of anhydrous form α. Heating of the monohydrate form resulted in a removal of the hydrated water to give anhydrous form α. Form γ and form α adsorbed water vapor rapidly under ordinary relative humidity conditions and transformed into the hemihydrate and monohydrate, respectively.

The present invention relates to the solid state physical properties of levofloxacin. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state Form of a compound may also affect its behavior on compaction and its storage stability.

These practical physical characteristics are influenced by the conformation and orientation of molecules in the unit cell, which defines a particular polymorphic Form of a substance. The polymorphic Form may give rise to thermal behavior different from that of the amorphous material or another polymorphic Form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic Form may also give rise to distinct spectroscopic properties that may be detectable by powder X-ray crystallography, solid state C-NMR spectrometry and infrared spectrometry.

SUMMARY OF THE INVENTION

In one embodiment the present invention provides a process for the preparation of levofloxacin comprising reacting (S)-(-)-9,10-difluoro-3-methyl-7-oxo-2,3-dihydro-7H-pyrido [1,2,3-de][1,4]benzoxazine-6-carboxylic acid ("Compound I") with N-methyl piperazine to form levofloxacin, and recovering the levofloxacin. Compound I may react with N-methyl piperazine either in a polar solvent or as a neat mixture.

In another embodiment of the invention, novel crystal forms A, B, C, F, G, and H, and methods for their preparation are described. In one embodiment, a method for preparing a levofloxacin form comprises maintaining levofloxacin at an elevated temperature, adding a polar solvent; and recovering a levofloxacin form. Preferably, this method further comprises cooling and maintaining the levofloxacin-solvent mixture at a below-ambient temperature.

DETAILED DESCRIPTION OF THE INVENTION

One embodiment of the present invention provides a process for preparing levofloxacin. In some embodiments, yields from about 70% to about 85%, or more, of purified levofloxacin are achieved. As used herein, "crude" and "purified" are relative terms meaning less pure or more pure, respectively. Greater yields are obtainable by the present invention, vis-a-vis prior art processes, due at least in part to the use of highly concentrated mixtures.

Unless indicated otherwise, the terms "levofloxacin" and "levofloxacin form" include the salts, hydrates, solvates and physiologically functional derivatives of levofloxacin. The term also includes all polymorphous forms of levofloxacin to the extent that they are not considered to be salts, hydrates, solvates or physiologically functional derivatives of levofloxacin.

One embodiment of the present invention provides a process for preparing levofloxacin comprising reacting (S)-(−)-9,10-difluoro-3-methyl-7-oxo-2,3-dihydro-7H-pyrido[1,2,3-de] [1,4] benzoxazine-6-carboxylic acid ("Compound I") with N-methyl piperazine in a polar solvent, preferably at an elevated temperature, to form levofloxacin. The elevated temperature is preferably about 70-120° C. The levofloxacin can then be precipitated and recovered using techniques well known in the art. As used herein, the term "precipitated" includes the formation of a solid in a solution or an increase in the amount of solid in a slurry. The preparation of Compound I is described, for example, in U.S. Pat. No. 4,382,892, which is incorporated herein by reference.

A suitable polar solvent is any that is capable of dissolving levofloxacin. Preferably, the polar solvent is dimethylsulfoxide (DMSO), an alcohol (preferably isobutanol), a ketone, propylene-glycol-monomethyl-ether (PGME) or dimethyl acetamide (DMA). As used herein, the term "polar solvent" is intended as a relative term to mean relatively more polar than another solvent.

In one embodiment, the volume of solvent is from about 14 ml to about 4 ml per gram of Compound I. In this embodiment, the solvent is preferably selected from the group consisting of isobutanol and PGME. In an alternative embodiment, the volume of solvent is less than about 3 ml per gram of the compound of Compound I. In this latter embodiment, the solvent is preferably selected from the group consisting of DMSO and DMA. Advantageously, short reaction times are needed to obtain high yields with DMSO.

If DMSO is used as the solvent, the preferred volume of solvent is up to about 3 ml solvent/g compound, more preferably about 0.5 to about 3 ml solvent/g compound, but more could be used. If PGME is used as the solvent, the preferred volume of solvent is about 4 to about 14 ml solvent/g compound, but more could be used.

Optionally, the process of the invention may further comprise adding an anti-solvent to the solvent after the reacting step to increase yield. As used herein, the term "anti-solvent" means a liquid in which levofloxacin is poorly soluble such that the addition of an anti-solvent to a solvent reduces the solubility of a levofloxacin. Preferably, the anti-solvent is one or more of the following: n-heptane, hexane, isopropyl alcohol, isopropyl alcohol in water (about 5% isopropyl alcohol or greater), butanol, acetonitrile, methyl ethyl ketone, or DMSO/water. When the solvent is propylene glycol monomethyl ether or isobutanol, the preferred antisolvent is heptane or hexane. When the solvent is DMSO, the preferred antisolvent is isopropanol.

In another embodiment, Compound I reacts with N-methyl piperazine as a neat mixture. In this embodiment, Compound I is preferably dissolved in a suspension of the N-methyl piperazine.

In one embodiment, the N-methyl piperazine is in molar excess over Compound I. Preferably, the molar excess is from about 2 to about 4 times. More preferably, the molar excess is from about 2 to about 2.5 times.

The preferred duration of the reacting step will depend on balancing the desire for the reaction to go to completion, which in turn depends on the reaction conditions, particularly the choice of solvent and the temperature, while maximizing efficiency and/or minimizing side reactions and/or degradation. For example, the reacting step is typically performed for a time period from about 1 h to about 24 h when a solvent is used. When the reaction is performed as a neat mixture, the time period for the reaction may be less than 1 h.

The reacting step may be performed at a temperature as high as about 110° C. to about 120° C. or higher. When the reaction is performed as a neat mixture, the reacting step is preferably performed at about the reflux temperature.

Preparation of Levofloxacin Forms

In another embodiment of the invention, a method for preparing a levofloxacin form comprises maintaining levofloxacin at a first elevated temperature, preferably in a first solvent; adding a polar solvent; and recovering a levofloxacin form. Preferably, this method further comprises cooling and maintaining the levofloxacin-solvent mixture at a below-ambient temperature.

The first solvent is a polar solvent capable of dissolving levofloxacin and preferably having a relatively high boiling point. Examples include PGME, DMA and DMSO. The levofloxacin may be heated to a first elevated temperature. However, it is preferable that the levofloxacin is first synthesized, such as by reacting Compound I with N-methyl piperazine, described above, and the reaction mixture is then brought directly to the second elevated temperature that is suitable for adding the polar solvent. The first elevated temperature depends on the particular solvent, but is generally in the range of about 70° C. to about 120° C., preferably about 80° C. to about 85° C. The second elevated temperature depends on the particular polar solvent, but is generally in the range of about 60° C. to about 80° C., preferably about 75° C. to about 79° C.

The polar solvent is added to the levofloxacin, preferably slowly, at the second elevated temperature. The polar solvent is preferably added over about 2 h. Optionally, the mixture is maintained, preferably with stirring or other agitation, for an additional period of time.

Recovering the levofloxacin typically includes cooling the mixture to precipitate the levofloxacin followed by filtration.

For the preparation of levofloxacin hemihydrate, the polar solvent comprises water, preferably a mixture of isopropanol and water, more preferably about 3% to about 4% (v/v) water. In this embodiment, the first elevated temperature is preferably about 80° C. and the second elevated temperature is preferably about 75° C. Preferably, the polar solvent is added dropwise over about 2 hours. Following the adding step, the levofloxacin-polar-solvent mixture is slowly cooled to a below-ambient temperature, preferably in the range of about 0° C. to about 20° C., more preferably about 5° C. Preferably, the cooling step occurs over about 1 to about 10 hours, more preferably about 4 hours. Preferably, the below-ambient temperature is maintained for an additional about 2 hours.

For the preparation of Form C, the polar solvent preferably comprises isopropanol. In this embodiment, the first elevated temperature is preferably about 85° C. and the second elevated temperature is preferably about 79° C. Preferably, the polar solvent is added dropwise over about 2 hours followed by an additional about 2 hours at this temperature.

For the preparation of Form A, the polar solvent preferably comprises isopropanol. In this embodiment, the first elevated temperature is preferably about 80° C. and the second elevated temperature is preferably about 75° C. Following the adding step, the levofloxacin-polar-solvent mixture is slowly cooled to a below-ambient temperature, preferably in the range of about 0° C. to about 20° C., more preferably about 5° C. Preferably, the cooling step occurs over about 1 to about 10 hours, more preferably about 4 hours. Preferably, the below-ambient temperature is maintained for an additional about 2 hours.

For the preparation of Forms G and B, the polar solvent preferably comprises isopropanol. In this embodiment, the first elevated temperature is preferably about 80° C. and the second elevated temperature is preferably about 75° C. Following the adding step, the levofloxacin-polar-solvent mixture is slowly cooled to a below-ambient temperature, preferably in the range of about 0° C. to about 20° C., more preferably about 5° C. Preferably, the cooling step occurs over about 1 to about 10 hours, more preferably about 4 hours. Preferably, the below-ambient temperature is maintained for an additional about 11 hours. Preferably, the precipitate is filtrated then dried. To obtain Form G, drying occurs at a third elevated temperature for about 3 to about 6 hours and a fourth elevated temperature for about 3 hours. The third elevated temperature is preferably about 40° C. and the fourth elevated temperature is preferably about 60° C. To obtain Form B, drying occurs at a third elevated temperature for at least about 20 hours, preferably about 21 hours, and a fourth elevated temperature for at least about 6 hours. The third elevated temperature is preferably about 40° C. and the fourth elevated temperature is preferably about 60° C.

For the preparation of Form H, the polar solvent comprises a mixture of isopropanol and water, more preferably about 0.3% to about 0.4% (v/v) water. In this embodiment, the first elevated temperature is preferably about 80° C. and the second elevated temperature is preferably about 75° C. Preferably, the polar solvent is added dropwise over about 1 hour. Following the adding step, the levofloxacin-polar-solvent mixture is preferably maintained at the second elevated temperature for about 2 hours. The mixture is then slowly cooled to a below-ambient temperature, preferably in the range of about 0° C. to about 20° C., more preferably about 5° C. Preferably, the cooling step occurs over about 1 to about 10 hours, more preferably about 4 hours. Preferably, the below-ambient temperature is maintained for an additional about 12 hours.

In another embodiment of the invention, a method for preparing a levofloxacin form comprises maintaining a first mixture of levofloxacin and a polar solvent at a first elevated temperature for about 4 hours or more, preferably at least 4.5 hours, cooling the first mixture to a second elevated temperature, adding additional polar solvent to the cooled first mixture to form a second mixture, maintaining the second mixture at a third elevated temperature until complete dissolution of the levofloxacin, optionally adding additional polar solvent to the second mixture during the maintaining step, cooling the second mixture to form a levofloxacin form, and recovering the levofloxacin form.

For the preparation of Form F, the polar solvent comprises isobutyl alcohol. In this embodiment, the first and third elevated temperatures are preferably reflux and the second elevated temperature is preferably about 80° C. Preferably, the minimum amount of the polar solvent that is sufficient to completely dissolve the levofloxacin is added to the second mixture. The second mixture is slowly cooled to a below-ambient temperature, preferably in the range of about −5° C. to about 20° C., more preferably about 5° C. Preferably, the cooling step occurs over about 1 to about 10 hours, more preferably about 1.5 hours.

Another embodiment of the invention is a pharmaceutical composition comprising a therapeutically effective amount of Forms A, B, C, F, G, H, or combinations thereof, and, optionally, a pharmaceutically acceptable carrier.

Another embodiment of the invention is a method for preparing a levofloxacin hemihydrate comprising storing one or more forms selected from the group consisting of Forms A, B, C, F, G, and H for an amount of time sufficient for the one or more forms to convert to a levofloxacin hemihydrate by the absorption of atmospheric water. For example, Forms A, B, C, F, G and H were converted to hemihydrate after 7-29 days of storing in a closed bottle at RT. The conversion to hemihydrate was faster (about 24 h) when keeping the sample in an open bottle.

Another embodiment of the invention is a method for preparing a levofloxacin form. (S)-(−)-9,10-difluoro-3-methyl-7-oxo-2,3-dihydro-7H-pyrido[1,2,3-de] [1,4]benzoxazine-6-carboxylic acid is reacted with N-methyl piperazine at an elevated temperature to form levofloxacin. The levofloxacin is then precipitated and maintained at a first elevated temperature in a first solvent. A polar solvent is added to precipitate the levofloxacin Form C, Form A, Form G, Form B, Form H, Form F, or the hemihydrate form, which can then be recovered by known means, such as filtration.

Physical Characterization of Levofloxacin Forms

TABLE 1

| | XRD characteristic peaks | |
|---|---|---|
| Crystal Form | XRD characteristic peaks (±0.3 deg. 2θ) | Additional XRD peaks (deg. 2θ) |
| A | 5.5, 11.3, 12.6, 18.8 | 2.9, 8.1, 10.8, 15.9, 16.1, 20.7, 21.5, 21.9, 23.2, 25.7, 29.4, 29.7 |

TABLE 1-continued

XRD characteristic peaks

| Crystal Form | XRD characteristic peaks (±0.3 deg. 2θ) | Additional XRD peaks (deg. 2θ) |
|---|---|---|
| B | 15.2, 15.8, 25.5, 25.8 | 5.3, 6.0, 6.7, 9.7, 13.1, 19.4, 20.0, 26.3, 26.7 |
| C | 12.2, 17.6, 18.0, 21.7, 22.4, 23.4 | 7.8, 10.8, 15.6, 17.2, 20.0, 20.6, 23.9, 24.5, 27.5, 27.8 |
| F | 11.9, 17.8, 18.4 | 5.3, 6.0, 6.7, 9.7, 10.6, 13.2, 13.4, 13.7, 15.5, 15.9, 19.4, 20.1, 25.3, 26.4, 26.8 |
| G | 5.3, 6.7, 13.1, 13.4, 26.4, 26.7 | 2.8, 9.9, 16.1, 18.7, 19.6, 20.1, 21.5, 29.6, 33.1, 33.8, 34.5, 35.0 |
| H | 4.9, 5.2, 5.5, 18.7 | 2.8, 6.7, 8.1, 10.7, 13.4, 16.1, 18.7, 20.1, 20.7, 21.4, 29.6, 35.1 |

DTG thermograms were performed on Shimadzu DTG-50, Heating rate: 10° C./min. The melting point was determined by an endothermic peak in the DTA curve to be about 225-230° C. for all the discussed crystal forms. The main differences in the DTA and TGA curves were observed in the temperature range of up to 160° C.

Thermal Analysis of Levofloxacin Forms

Figure 1:
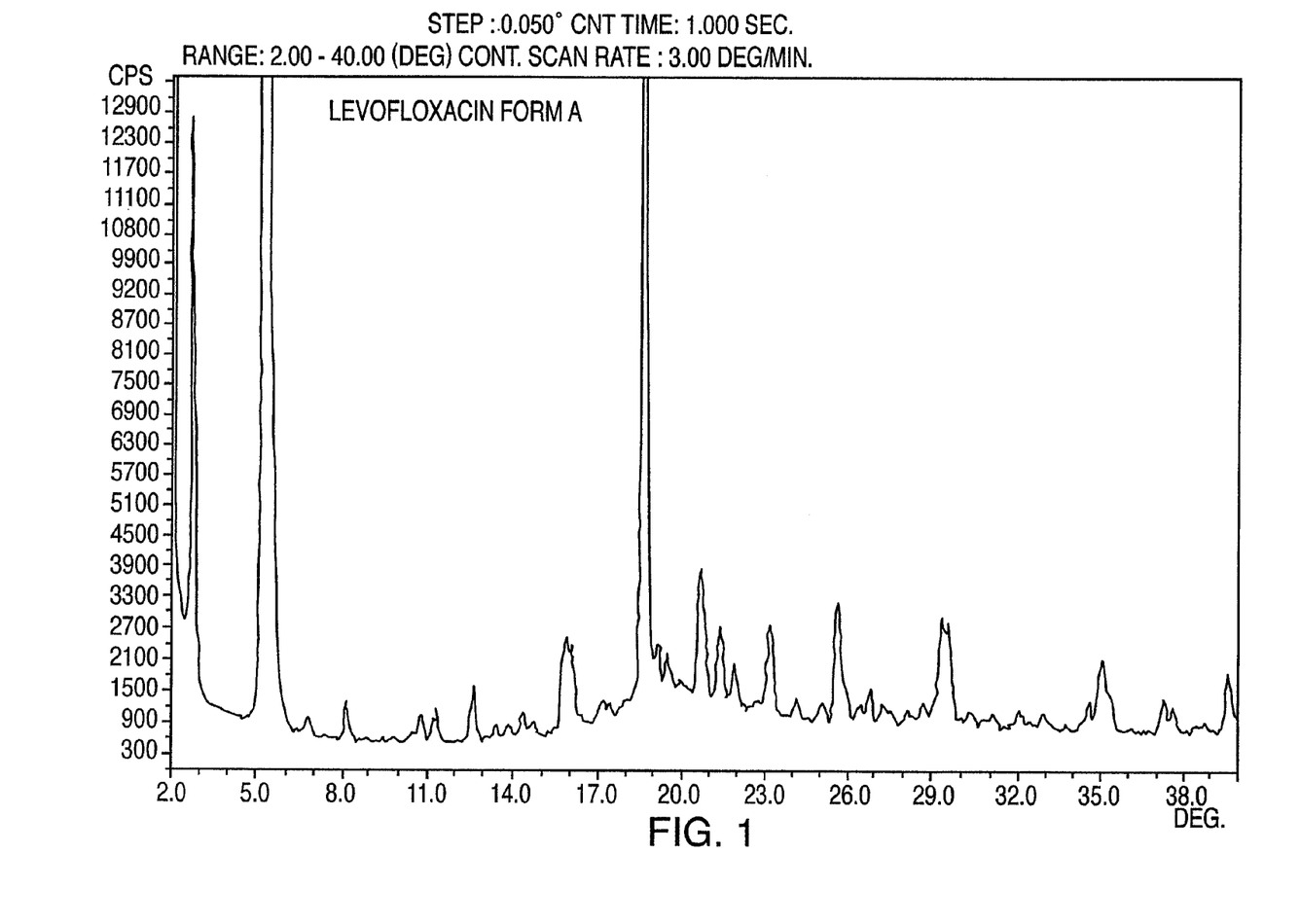
FIG. 1 is an XRD diffractograms of novel levofloxacin crystal form A.
Figure 2:
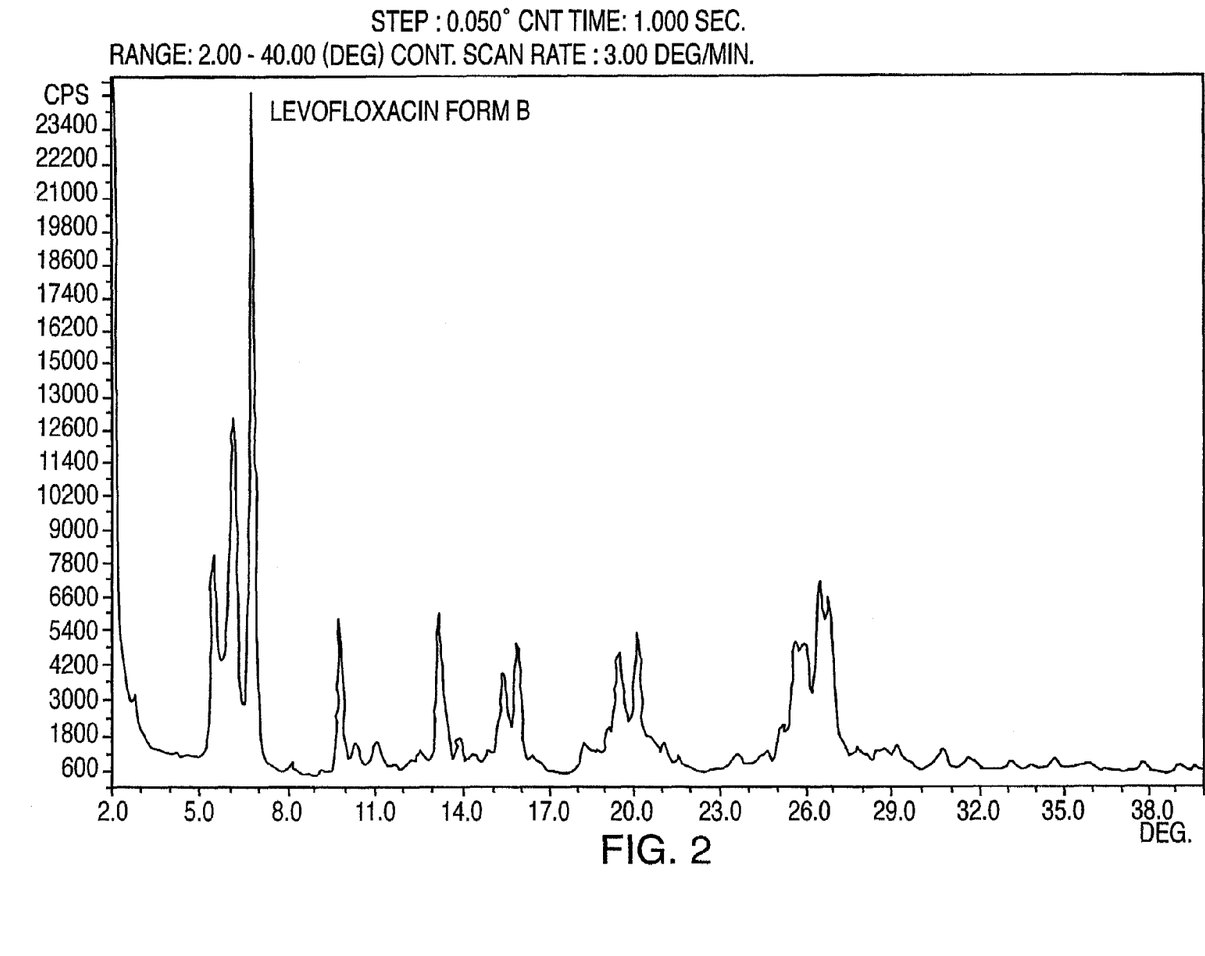
FIG. 2 is an XRD diffractograms of novel levofloxacin crystal form B.
Figure 3:
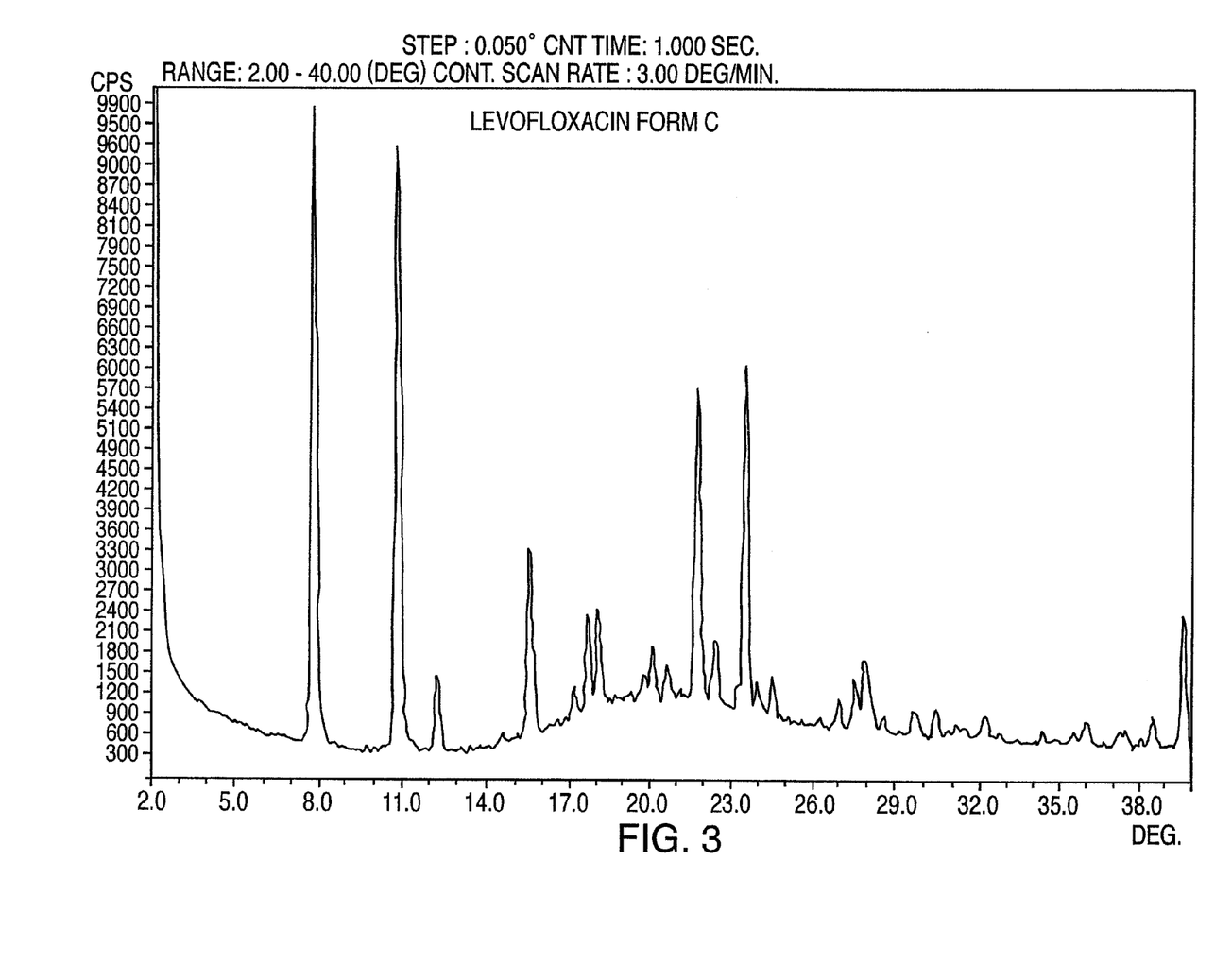
FIG. 3 is an XRD diffractograms of novel levofloxacin crystal form C.
Figure 4:
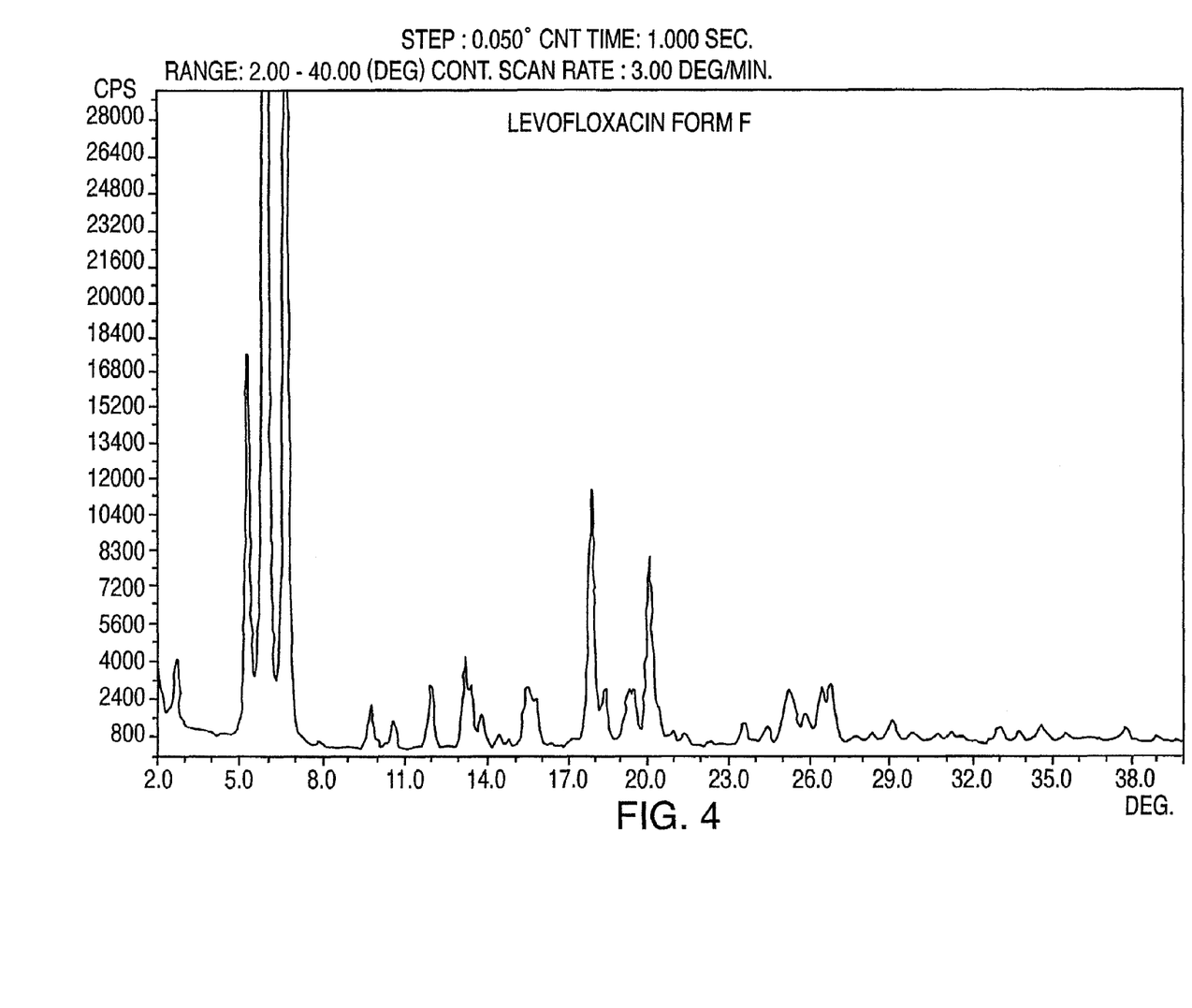
FIG. 4 is an XRD diffractograms of novel levofloxacin crystal form F.
Figure 5:
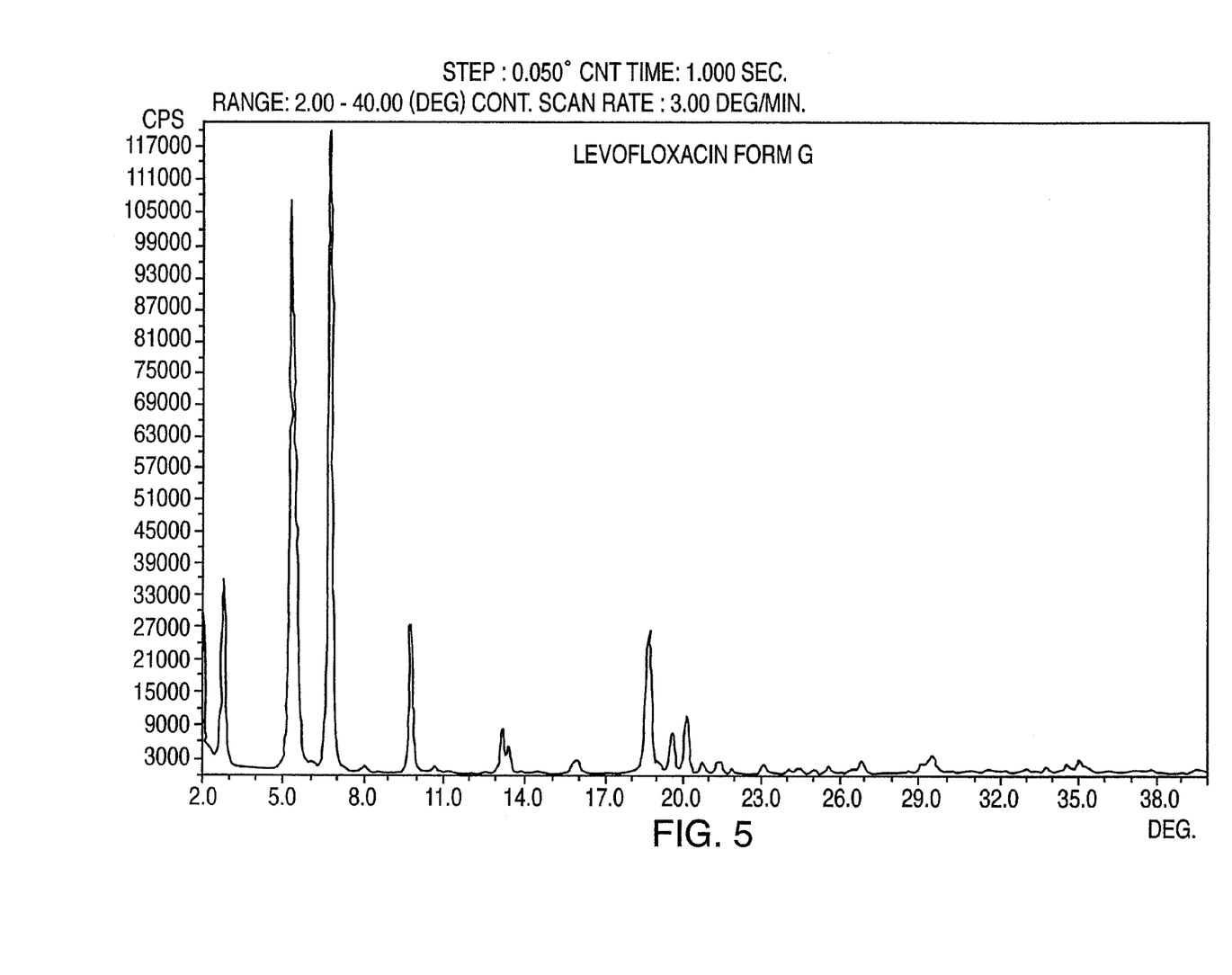
FIG. 5 is an XRD diffractograms of novel levofloxacin crystal form G.
Figure 6:
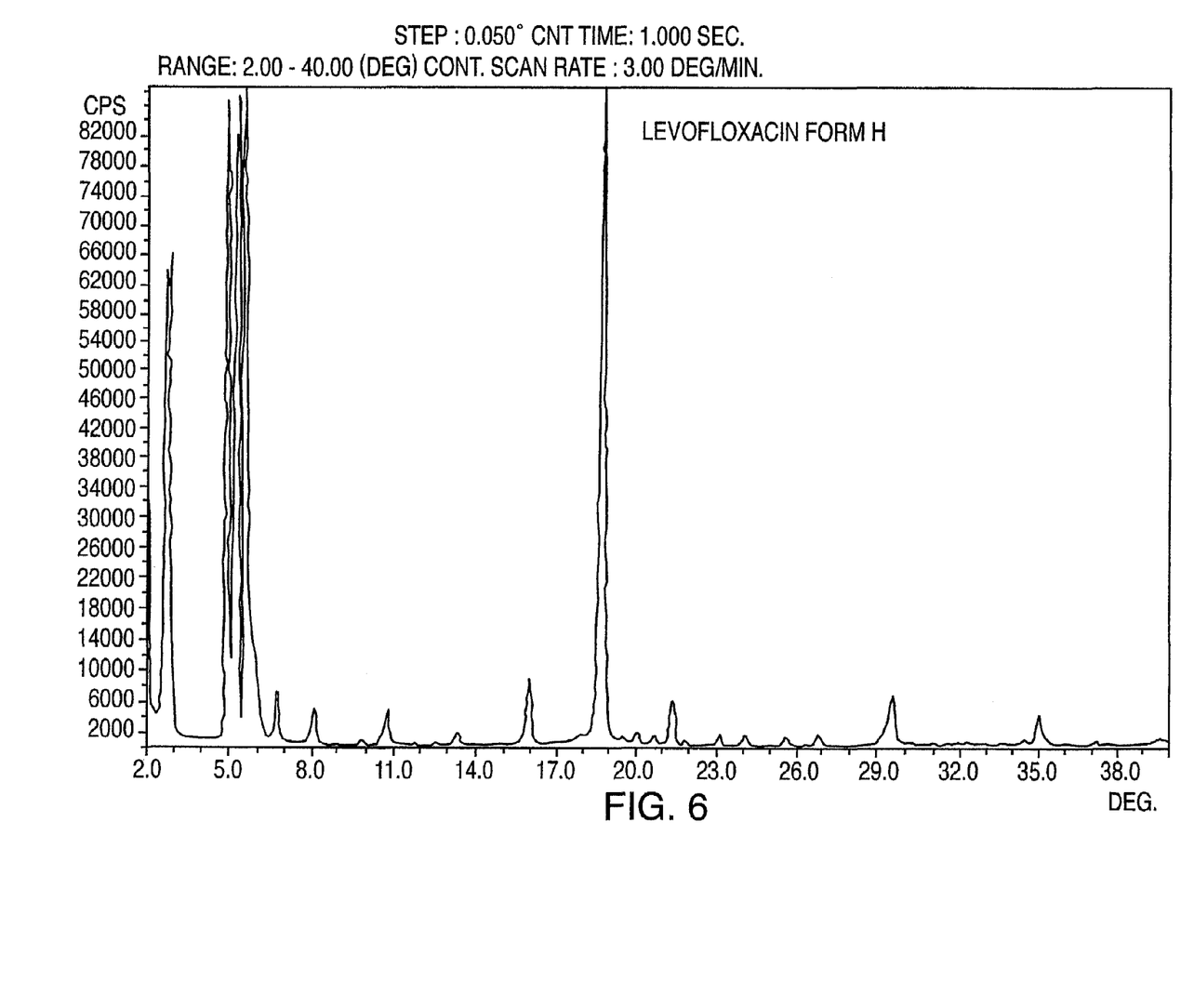
FIG. 6 is an XRD diffractograms of novel levofloxacin crystal form H.
Figure 7:
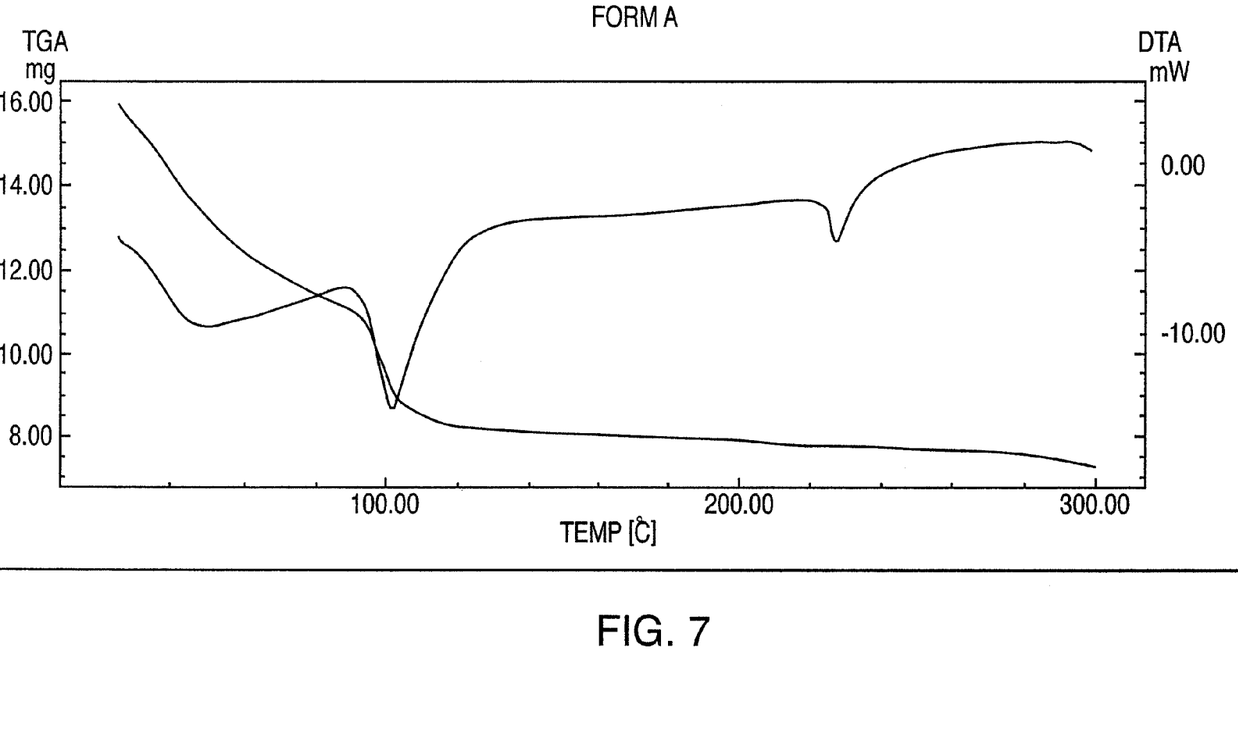
FIG. 7 is a DTG thermogram of novel levofloxacin crystal form A.

Levofloxacin novel form A is characterized by an endothermic peak at about 100° C. A weight loss step of about 18-22% is observed in this temperature range due to the removal of solvent from the crystals. See FIG. 7.

Figure 8:
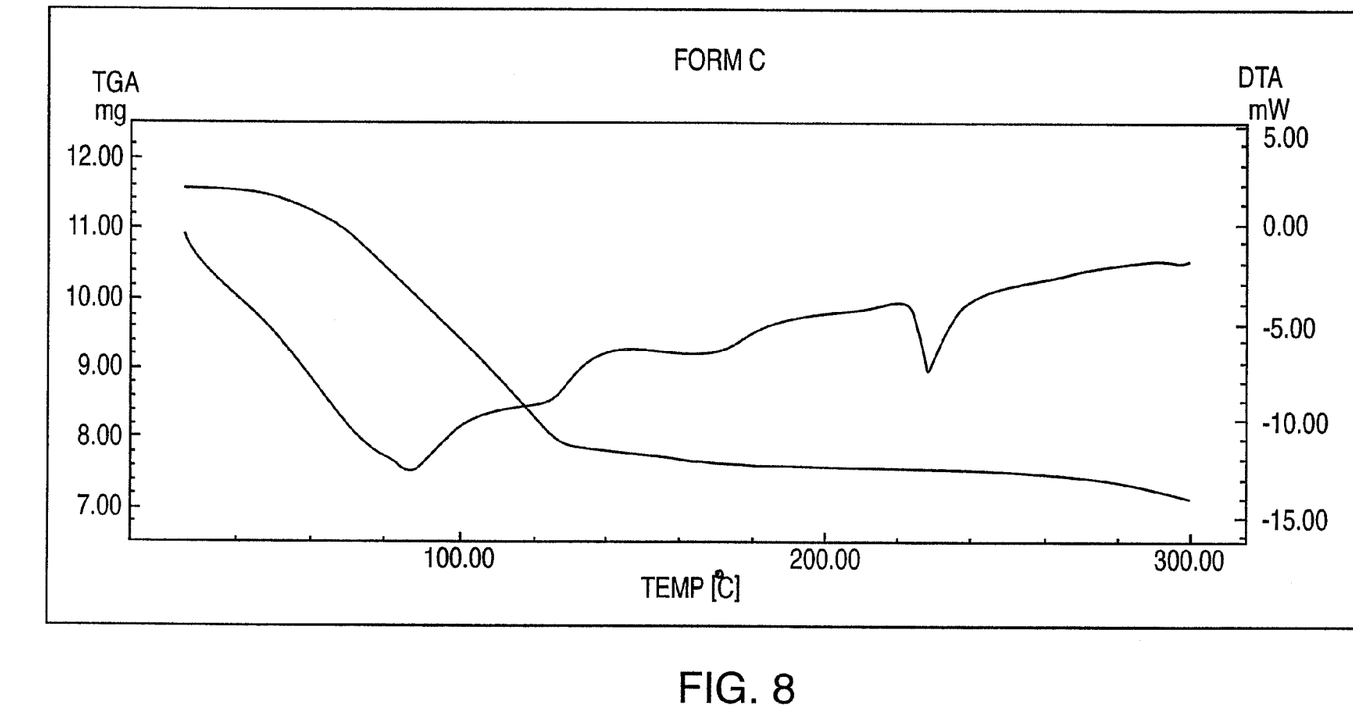
FIG. 8 is a DTG thermogram of novel levofloxacin crystal form C.

Levofloxacin novel form C is characterized by high content of DMSO (30-50%) and water content of about 3.5% by KF. See FIG. 8.

Figure 9:
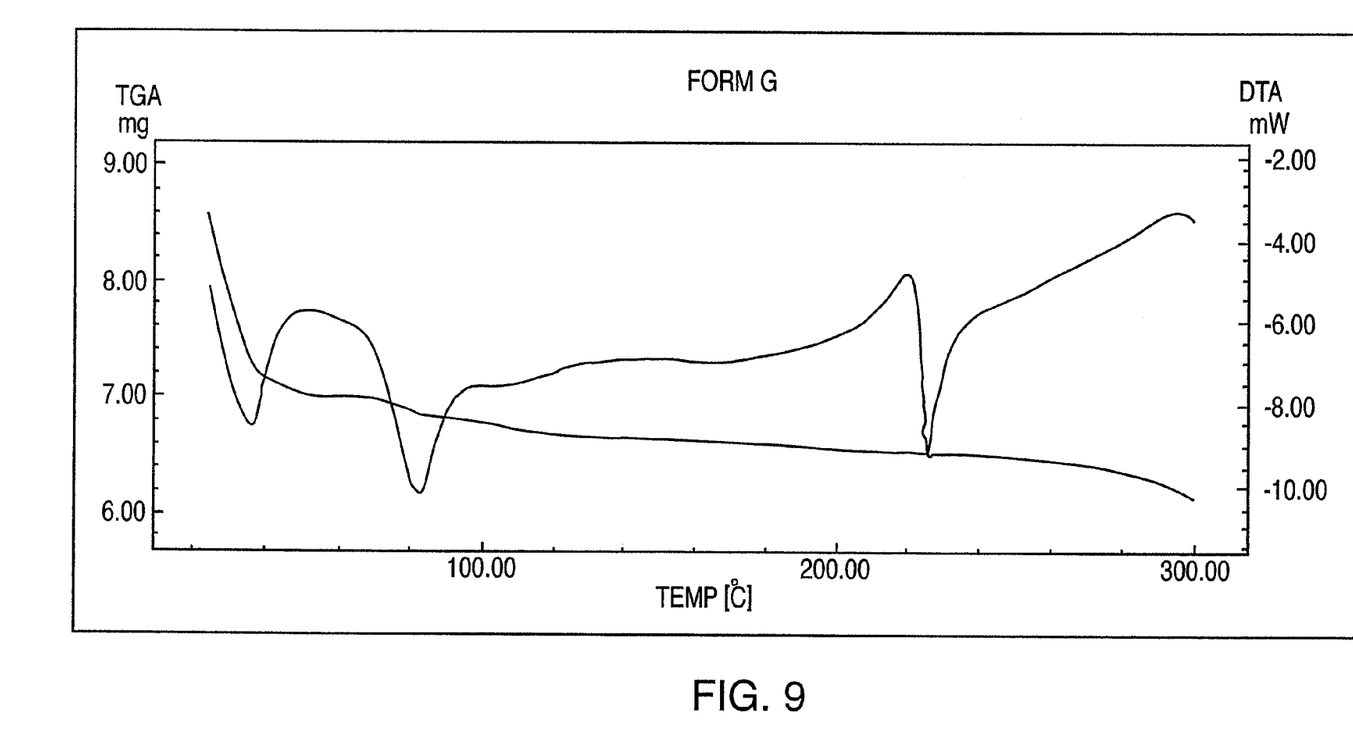
FIG. 9 is a DTG thermogram of novel levofloxacin crystal form G.

Levofloxacin novel form G is characterized by two endothermic peaks at about 82° C. and about 103° C. A weight loss step 3-6% is observed in this temperature range. This weight loss value is in coincident with the DMSO content in the sample. See FIG. 9.

Figure 10:
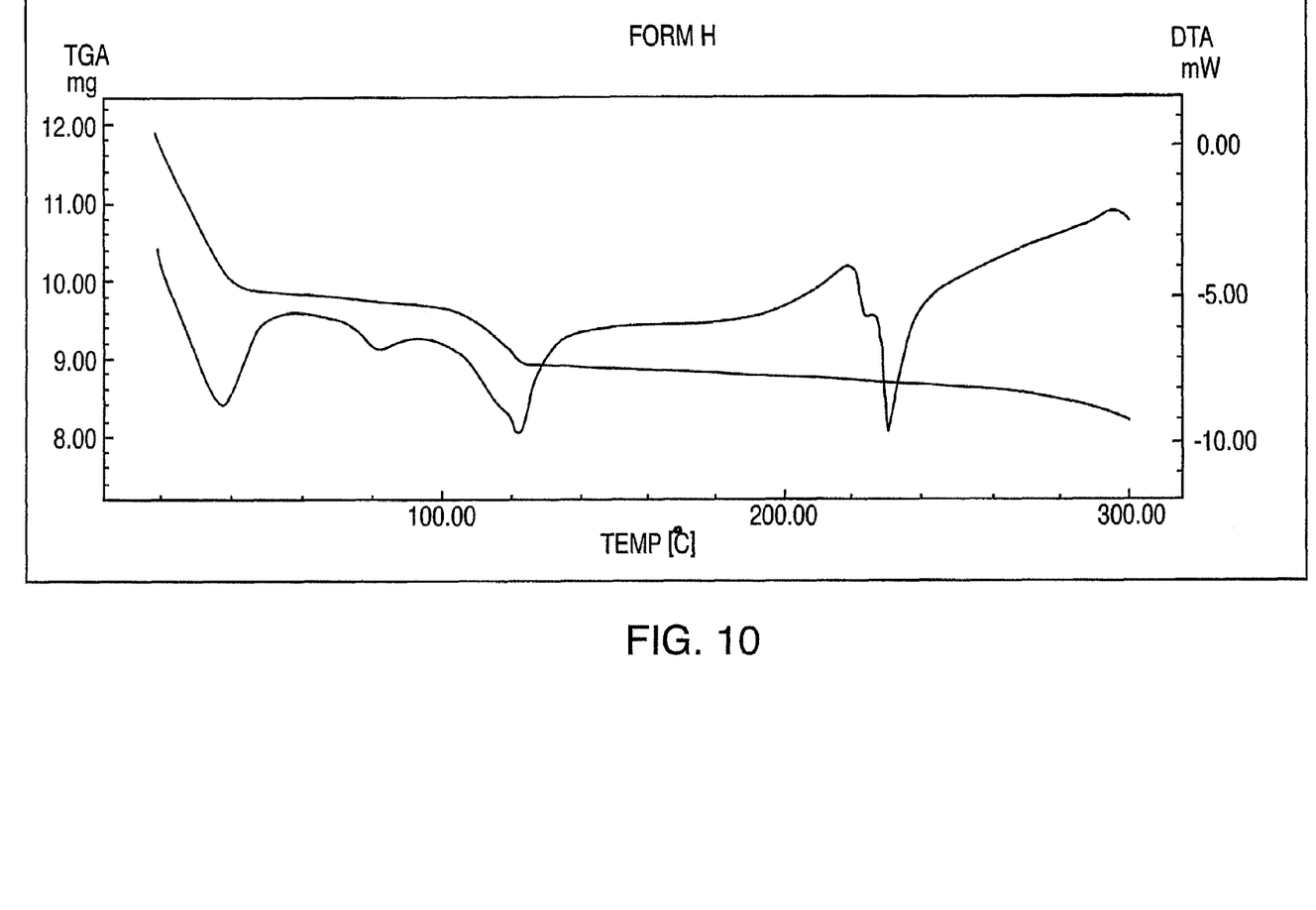
FIG. 10 is a DTG thermogram of novel levofloxacin crystal form H.

Levofloxacin novel form H is characterized by an endothermic peak at about 122° C. A weight loss step of about 8% is observed in the range of 60 to 150° C. This weight loss percent is equal to the expected value corresponds to Levofloxacin:IPA solvate in the ratio of 1:0.5, which is 7.7%. See FIG. 10.

The function and advantages of these and other embodiments of the present invention will be more fully understood from the examples below. The following examples are intended to illustrate the benefits of the present invention, but do not exemplify the full scope of the invention.

EXAMPLES

Example 1

Synthesis of Levofloxacin in DMSO 5 g (17.8 mmole) of (S)-(−)-9,10-difluoro-3-methyl-7-oxo-2,3-dihydro-7H-pyrido [1,2,3-de][1,4]benzoxazine-6-carboxylic acid was put in suspension in 2.5 mL of DMSO and 4.2 mL (37.9 mmole) of N-methyl piperazine. The reaction mixture was heated to 120° C. and the suspension became soluble. After 2.5 h the reaction was completed. The mixture was then cooled to 70° C. and isopropanol (25 mL) was then added at this temperature. The reaction mixture was slurried for 1 h at ambient temperature, filtered, and dried overnight to obtain 5.86 g (91.3%) of levofloxacin.

Example 2

Synthesis of Levofloxacin in PGME 3 g (10.67 mmole) of (S)-(−)-9,10-difluoro-3-methyl-7-oxo-2,3-dihydro-7H-pyrido [1,2,3-de] [1,4]benzoxazine-6-carboxylic acid was put in suspension in 30 mL of PGME and 4.75 mL (43 mmole) of N-methyl piperazine. The reaction mixture was heated to reflux for 23 hours until completion of the reaction. During that time, the reaction mixture became soluble. The mixture was then cooled to 90° C. and n-Heptane (10 mL) was added at this temperature. The reaction mixture was then cooled to 0° C. and the precipitation occurred around 65° C. The reaction was left at 0° C. for 3 hours, filtrated under vacuum and dried overnight to obtain 2.98 g (77.3%) of levofloxacin.

Example 3

Synthesis of Levofloxacin in Isobutanol 3 g (10.67 mmole) of (S)-(−)-9,10-difluoro-3-methyl-7-oxo-2,3-dihydro-7H-pyrido [1,2,3-de] [1,4]benzoxazine-6-carboxylic acid was put in suspension in 21 mL of isobutanol and 4.75 mL (43 mmole) of N-methyl piperazine. The reaction mixture was heated to reflux for 6 hours, then slurried at ambient temperature for 60 hours and heated again to reflux for 7 hours until completion of the reaction. During that time, the reaction mixture became soluble at reflux temperature. The mixture was then cooled to 0° C., filtered under vacuum, washed with 7 mL isobutanol and 10 mL n-heptane, and dried overnight to obtain 2.83 g (77.3%) of levofloxacin.

Example 4

Synthesis of Levofloxacin (Neat)

5 g (17.79 mmole) of (S)-(−)-9,10-difluoro-3-methyl-7-oxo-2,3-dihydro-7H-pyrido [1,2,3-de][1,4]benzoxazine-6-carboxylic acid was put in suspension in 6.8 mL (0.06 mole) of N-methyl piperazine. The reaction mixture was heated to reflux for 40 minutes until completion of the reaction. The mixture was then cooled to 80° C. IPA (10 mL) and n-heptane (10 mL) were added at this temperature. The solid was filtrated under vacuum and rinsed with n-heptane. The mother liquor also gave a precipitate after addition of n-heptane. Both precipitates were filtrated under vacuum and dried overnight to yield 4.9 g (76%) levofloxacin.

Example 5

Synthesis of Levofloxacin in DMA 10 g (35.6 mmole) of (S)-(−)-9,10-difluoro-3-methyl-7-oxo-2,3-dihydro-7H-pyrido [1,2,3-de] [1,4]benzoxazine-6-carboxylic acid was put in suspension in 5 mL of DMA (dimethyl acetamide) and 8.3 mL (75 mmole) of N-methyl piperazine. The reaction mixture was heated to 110° C. until the complete conversion of the starting material, about 1.5 h. The reaction mixture was then cooled to 80° C. and 60 ml of isopropyl alcohol was added. The reaction mixture was then slurried for 3 hours at ambient temperature filtered under vacuum, washed with 40 ml IPA and dried in vacuum oven overnight to obtain 11.48 g (89.3%) of levofloxacin.

Example 6

Synthesis of Hemihydrate

In 1 liter reactor equipped with a mechanical stirrer, a condenser and a thermometer, heated at 80° C., was charged 87.5 g (0.31 mole) of (S)-(−)-9,10-difluoro-3-methyl-7-oxo-2,3-dihydro-7H-pyrido[1,2,3-de][1,4]benzoxazine-6-carboxylic acid, 61.3 mL DMSO and 86.3 mL (0.77 mole) of N-methylpiperazine. The slurry was stirred at a rate of 250 rpm under nitrogen atmosphere at 80° C. until completion of the reaction (monitoring by HPLC). Then the slurry was cooled to 75° C. and a mixture of isopropanol (675 mL) and water (25 mL) was added dropwise at this temperature during 2 hours. The slurry was then cooled to 5° C. during 4 hours, maintained at this temperature for 2 hours and filtrated under vacuum at this temperature. The solid was then washed with 175 mL of isopropanol (2 rinses) and dried under vacuum to obtain levofloxacin hemihydrate.

Example 7

Synthesis of Form C

Preparation

A 1 liter reactor equipped with mechanical stirrer, condenser and thermometer, was heated to 85° C., charged with (S)-9,10,difluoro-3methyl-7-oxo-2,3-dihydro-7H-pyri do[1,2,3-de][1,4]benzoxazine-6-carboxylic acid (87.5 g), DMSO (61.3 ml) and N-methylpiperazine (86.3 ml). The slurry was stirred at a rate of 250 rpm under nitrogen atmosphere. The heating was continued for 4.5 hours until completion of the reaction (monitoring by HPLC). Then the slurred mixture was cooled to 79° C. and isopropanol (700 ml) was added dropwise at this temperature during 2 hours and stirred at this temperature for an additional 2 hours. At the end of the addition, a sample was filtrated under vacuum and washed with isopropanol

Example 8

Synthesis of Form A

Preparation

A 1 liter reactor equipped with mechanical stirrer, condenser and thermometer, was heated to 80° C., charged with (S)-9,10,difluoro-3methyl-7-oxo-2,3-dihydro-7H-pyri do[1,2,3-de][1,4]benzoxazine-6-carboxylic acid (87.5 g), DMSO (61.3 ml) and N-methylpiperazine (86.3 ml). The slurry was stirred at a rate of 250 rpm under air atmosphere. The heating was continued for 4.5 hours until completion of the reaction (monitoring by HPLC). Then the slurred mixture was cooled to 75° C., and isopropanol (700 ml) was added dropwise at this temperature during 2 hours. A sample was taken for XRD analysis. The mixture was maintained with stirring for 2 hours at this temperature. Then the reaction mixture was cooled during 4 hours until 5° C. and maintained with the stirring for 2 hours at this temperature. At the end, the reaction mixture was filtrated under vacuum and washed with isopropanol (175 ml) to obtain 171 g of wet material (106.8 g dry material, 92.7%).

Example 9

Synthesis of Form G and Form B

Preparation

A 1 liter reactor equipped with mechanical stirrer, condenser and thermometer, was heated to 80° C., charged with (S)-9,10,difluoro-3methyl-7-oxo-2,3-dihydro-7H-pyri do[1,2,3-de][1,4]benzoxazine-6-carboxylic acid (87.5 g), DMSO (61.3 ml) and N-methylpiperazine (86.3 ml). The slurry was stirred at a rate of 250 rpm under nitrogen atmosphere. The heating was continued for 4.5 hours until completion of the reaction. Then the slurred mixture was cooled to 75° C. and isopropanol (700 ml) was added dropwise at this temperature during 2 hours.

At the end of the addition the stirring was maintained for 2 hours at 75° C., then cooled during 4 hours until 5° C. and maintained with stirring for 11 hours at this temperature. The slurry was filtrated under vacuum and washed with isopropanol (175 ml) to obtain 149 g of wet material.

The wet material was divided in two portions for drying. The first portion was dried under vacuum with stirring at 40° C. for 21 hours and the second fraction was dried under vacuum with stirring at 60° C. for 21 hours. Levofloxacin Form G was resulted after drying at 40° C. for 3 or 6 hours, and after drying at 60° C. for 3 hours. Levofloxacin Form B was resulted after drying at 40° C. for 21 hours, and after drying at 60° C. for 6, 9 and 21 hours.

Example 10

Synthesis of Form H

Preparation

A 1 liter reactor equipped with mechanical stirrer, condenser and thermometer, was heated to 80° C., charged with (S)-9,10,difluoro-3methyl-7-oxo-2,3-dihydro-7H-pyri do[1,2,3-de] [1,4]benzoxazine-6-carboxylic acid (87.5 g), DMSO (61.3 ml) and N-methylpiperazine (86.3 ml). The slurry was stirred at a rate of 250 rpm under nitrogen atmosphere. The heating was continued for 4.5 hours until completion of the reaction (monitoring by HPLC). Then the slurred mixture was cooled to 75° C. and isopropanol (697.5 ml) mixed with $H_2O$ (2.5 ml) was added dropwise at this temperature during 1 hour. At the end of the addition the stirring was maintained for 2 hours and then cooled during 4 hours until 5° C. The stirring was maintained for 12 hours at this temperature. The reaction mixture was then filtrated under vacuum and washed with isopropanol (175 ml) to obtain 150 g of wet material.

Example 11

Synthesis of Form F

Preparation 4.0 g of Levofloxacin was put in a flask equipped with a condenser. Isobutyl alcohol (8 mL) was added and the mixture was heated to reflux temperature. After 15 minutes, the mixture was cooled to 80° C. and 4 mL of isobutyl alcohol was added. The mixture was then heated again to reflux temperature. Isobutyl alcohol (6 mL) was added until complete dissolution. The solution became clear and the mixture was cooled to 0° C. in 1.5 hour. The precipitate was then filtrated under vacuum, washed with isobutyl alcohol (4 mL) and dried under vacuum at 60° C.

Example 12

Time-Induced Conversion of Forms

A 1 liter reactor equipped with mechanical stirrer, condenser and thermometer, was charged with (S)-9,10,difluoro-3methyl-7-oxo-2,3-dihydro-7H-pyrido[1,2,3-de] [1,4] benzoxazine-6-carboxylic acid (87.5 g), DMSO (61.3 ml), N-methylpiperazine (86.3 ml) and $H_2O$ (0.44 ml). The slurry was then heated to 80° C. and stirred at a rate of 250 rpm under nitrogen atmosphere. The heating was continued for 4.5 hours until completion of the reaction. Then the slurred mixture was cooled to 75° C. and isopropanol (700 ml) was added dropwise at this temperature over 2 hours.

The mixture was then maintained with stirring for 2 hours at 75° C. The mixture was then cooled over 4 hours until 5° C., at which temperature the mixture was maintained with the stirring for 9 hours. The slurry was filtrated under vacuum and washed with isopropanol (175 ml) to obtain 147 g of wet polymorph H.

The wet material was exposed to the air at RT covered with paper (for protection). After 3, 6, 9 hours the polymorph of the wet samples was Form G. After 24 hours the wet sample was the hemihydrate polymorph.

Example 13

Conversion of Form H in a Slurry

A 1 liter reactor equipped with mechanical stirrer, condenser and thermometer, was heated to 80° C., charged with (S)-9,10,difluoro-3methyl-7-oxo-2,3-dihydro-7H-pyrido [1,2,3-de] [1,4]benzoxazine-6-carboxylic acid (87.5 g), DMSO (61.3 ml) and N-methylpiperazine (86.3 ml). The slurry was stirred at a rate of 250 rpm under nitrogen atmosphere. The heating was continued for 4.5 hours until completion of the reaction (monitoring by HPLC). Then the slurred mixture was cooled to 75° C. and isopropanol (697.5 ml) mixed with $H_2O$ (2.5 ml) was added dropwise at this temperature over 1 hour.

The mixture was then maintained with stirring for 2 hours. The mixtures was then cooled over 4 hours until 5° C., at which temperature it was maintained for 12 hours. The reaction mixture was then filtrated under vacuum and washed with isopropanol (175 ml) to obtain 150 g of wet polymorph H.

A first portion of the wet material was stirred in 5 v of acetonitrile at 75° C. for 2 h, then filtrated under vacuum. The polymorphism of the wet sample was Hemihydrate. A second portion of the wet material was exposed to the air at RT covered with paper (for protection).

After a few hours the polymorph of the wet samples was Hemihydrate.

Example 14

Conversion of Form G in a Slurry

A 1 liter reactor equipped with mechanical stirrer, condenser and thermometer, was charged with (S)-9,10,difluoro-3methyl-7-oxo-2,3-dihydro-7H-pyrido[1,2,3-de] [1,4] benzoxazine-6-carboxylic acid (87.5 g), DMSO (61.3 ml) and N-methylpiperazine (86.3 ml) at ambient temperature. The slurry was then heated to 80° C. and stirred at a rate of 250 rpm under nitrogen atmosphere. The heating was continued for 4 hours until completion of the reaction. Then the slurred mixture was cooled to 75° C. and isopropanol (679 ml) mixed with $H_2O$ (21 ml) was added dropwise at this temperature over 2 hours.

The mixtures was then maintained with stirring for 2 hours at 75° C. The mixture was then cooled over 4 hours until 5° C., at which temperature it was maintained with the stirring for 10 hours. The slurry was filtrated under vacuum and washed with isopropanol (175 ml) to obtain 166.5 g of wet polymorph G.

The wet material (162 g) was mixed with acetonitrile (486 ml). The slurry was stirred at 27° C. for 1 hour at a rate of 250 rpm. The slurry was then filtrated under vacuum and washed with acetonitrile (162 ml). The wet sample was the hemihydrate polymorph. The solid was dried in a vacuum oven at 40° C. for 6 hours. The dry Levofloxacin crude was the hemihydrate polymorph.

Example 15

Dry

A 1 liter reactor equipped with mechanical stirrer, condenser and thermometer, was charged with (S)-9,10,difluoro-3methyl-7-oxo-2,3-dihydro-7H-pyrido[1,2,3-de] [1,4] benzoxazine-6-carboxylic acid (87.5 g), DMSO (61.3 ml) and N-methylpiperazine (86.3 ml) at ambient temperature. The slurry was then heated to 80° C. and stirred at a rate of 250 rpm under nitrogen atmosphere. The heating was continued for 4.5 hours until completion of the reaction. Then the slurred mixture was cooled to 75° C. and isopropanol (700 ml) was added at once. At the end of the addition, the mixture was stirred at a rate of 300 rpm. The reaction mixture was cooled over 2 hours until 7° C. The stirring was maintained for 2 hours at this temperature and at a rate of 350 rpm. The reaction mixture was then filtrated under vacuum and washed with isopropanol (175 ml).

The wet material (162 g) was mixed with isopropanol (180 ml). The slurry was stirred at 40° C. for 1 hour at a rate of 250 rpm. The slurry was then filtrated under vacuum and washed with isopropanol (60 ml). The polymorph of the wet sample was H.

The solid was dried in a vacuum oven at 60° C. for 14 hours to obtain 106 g (92%) of dry levofloxacin Form B.

Example 16

Dry

A 1 liter reactor equipped with mechanical stirrer, condenser and thermometer, was charged with (S)-9,10,difluoro-3methyl-7-oxo-2,3-dihydro-7H-pyrido[1,2,3-de][1,4] benzoxazine-6-carboxylic acid (87.5 g), DMSO (61.3 ml) and N-methylpiperazine (86.3 ml) at ambient temperature. The slurry was then heated to 80° C. and stirred at a rate of 250 rpm under nitrogen atmosphere. The heating was continued for 4.5 hours until completion of the reaction. Then the slurred mixture was cooled to 75° C. and isopropanol (700 ml) was added at once. At the end of the addition, the mixture was stirred at a rate of 300 rpm. The reaction mixture was cooled over 2 hours until 7° C. The stirring was maintained for 2 hours at this temperature and at a rate of 350 rpm. The reaction mixture was then filtrated under vacuum and washed with isopropanol (175 ml).

The wet material (162 g) was mixed with isopropanol (180 ml). The slurry was stirred at 40° C. for 1 hour at a rate of 250 rpm. The slurry was then filtrated under vacuum and was washed with isopropanol (60 ml). The polymorph of the wet samples was G.

The solid was dried in a vacuum oven at 60° C. for 14 hours to obtain 106 g (92%) of dry levofloxacin Form B.

Example 17

Preparation of Hemihydrate Using n-BuOH 1 g of levofloxacin crude was put in suspension in 7 ml of n-BuOH. The mixture was heated to reflux temperature until complete dissolution of the material. Then the solution was cooled to RT over a period of 2.5 hours. The precipitate was filtrated under vacuum, washed with n-BuOH and dried at 60° C. in a vacuum oven to give 810 mg (81%) of purified levofloxacin hemihydrate.

Example 18

Preparation of Hemihydrate Using ACN 1.5 g of levofloxacin crude was put in suspension in 10.5 ml of ACN. The mixture was heated to reflux temperature until complete dissolution of the material. Then the solution was cooled to 0° C. over a period of 20 minutes. The precipitate was filtrated under vacuum, washed with ACN (1.5 ml) and dried at 30° C. in a vacuum oven to give 1.15 g (77%) of purified levofloxacin (hemihydrate/monohydrate mixture). The purified levofloxacin contained approximately half the amount of desmethyl levofloxacin as that in the crude sample.

Example 19

Preparation of Hemihydrate Using DMSO/Water 1 g of levofloxacin crude was put in suspension in 1.5 ml of DMSO. The mixture was heated to 108° C. until complete dissolution of the material. Then $H_2O$ (7.5 ml) was added over 10 minutes and the mixture was cooled to RT. The precipitate was filtrated under vacuum, washed with 1 ml of a mixture DMSO:$H_2O$ 1:5 and dried at 60° C. in an air-flow oven to give 840 mg (84%) of purified levofloxacin hemihydrate.

Example 20

Preparation of Hemihydrate Using MEK 1.5 g of levofloxacin crude was put in suspension in 15 ml of MEK. The mixture was heated to reflux temperature until complete dissolution of the material. Then the solution was cooled to −5° C. over a period of 3 hours. The precipitate was filtrated under vacuum, washed with 1.5 ml of MEK and dried at 30° C. in a vacuum oven to give 840 mg (84%) of purified levofloxacin hemihydrate.

What is claimed is:

1. A method for preparing (S)-(−)-9-fluoro-2,3-dihydro-3-methyl-10-(4-methyl-1-piperazinyl)-7-oxo-7H-pyrido[1,2,3-de]-1,4-benzoxazine-6-carboxylic acid hemihydrate, comprising:
maintaining levofloxacin at a first elevated temperature in a first solvent, wherein the first solvent is a polar solvent capable of dissolving levofloxacin, wherein the polar solvent capable of dissolving levofloxacin is selected from the group consisting of dimethylsulfoxide (DMSO), isobutanol, n-BuOH, ketone, propylene-glycol-monomethyl-ether (PGME) and dimethyl acetamide (DMA);
adding water or a polar solvent comprising water to precipitate levofloxacin, wherein the polar solvent is selected from the group consisting of isopropyl alcohol (IPA), IPA/$H_2O$, BuOH, acetonitrile (ACN), methyl ethyl ketone (MEK), and DMSO/$H_2O$; and
recovering the (S)-(−)9,10-difluoro-3-methyl-7-oxo-2,3-dihydro-7H-pyrido[1,2,3-de][1,4]benzoxazine-6-carboxylic acid hemihydrate.

2. The method of claim 1, wherein the amount of the polar solvent comprising water is less than about 8 volumes/g starting material; and wherein the polar solvent comprising water is isopropanol comprising water.

3. The method of claim 2, wherein the recovering step comprises cooling a mixture comprising (S)-(−)-9,10-difluoro-3-methyl-7-oxo-2,3-dihydro-7H-pyrido[1,2,3-de][1,4]benzoxazine-6-carboxylic acid hemihydrate precipitate and the polar solvent comprising water to about 0° C. to about 20° C.; and
maintaining the mixture at 0° C. to about 20° C. for at least about 2 hours.

4. A method for preparing (S)-(−)-9,10-difluoro-3-methyl-7-oxo-2,3-dihydro-7H-pyrido[1,2,3-de][1,4]benzoxazine-6-carboxylic acid hemihydrate, comprising:
reacting (S)-(−)-9,10-difluoro-3-methyl-7-oxo-2,3-dihydro-7H-pyrido[1,2,3-de][1,4]benzoxazine-6-carboxylic acid with N-methyl piperazine at an elevated temperature to form levofloxacin;
maintaining the levofloxacin formed in the reacting step in a first solvent selected from the group consisting of dimethyl sulfoxide, isobutanol, n-BuOH, ketones, propylene-glycol- monomethyl ether and dimethyl acetamide;
adding water or a polar solvent comprising water to precipitate levofloxacin, wherein the polar solvent is selected from the group consisting of isopropyl alcohol (IPA), IPA/$H_2O$, )BuOH, acetonitrile (ACN), methyl ethyl ketone (MEK), and DMSO/$H_2O$; and
recovering the (S)-(−)-9,10-difluoro-3-methyl-7-oxo-2,3-dihydro-7H-pyrido[1,2,3-de][1,4]benzoxazine-6-carboxylic acid hemihydrate.

5. A method for preparing (S)-(−)-9,10-difluoro-3-methyl-7-oxo-2,3-dihydro-7H-pyrido[1,2,3 -de][1,4]benzoxazine-6-carboxylic acid hemihydrate comprising storing one or more forms selected from the group consisting of Forms A, B, C, F, G and H of levofloxacin for an amount of time sufficient for the one or more forms to convert to (S)-(−)- 9,10-difluoro-3-methyl-7-oxo-2,3-dihydro-7H-pyrido[1,2,3 -de][1,4]benzoxazine-6-carboxylic acid hemihydrate by the absorption of atmospheric water.

6. A method for preparing (S)-(−)-9,10-difluoro-3-methyl-7-oxo-2,3-dihydro-7H-pyrido[1,2,3-de][1,4]benzoxazine-6-carboxylic acid hemihydrate, comprising:
reacting (S)-(−)-9,10-difluoro-3-methyl-7-oxo-2,3-dihydro-7H-pyrido[1,2,3-de][1,4]benzoxazine-6-carboxylic acid with N-methyl piperazine at an elevated temperature to form levofloxacin;
precipitating the levofloxacin;
maintaining the levofloxacin at a first elevated temperature in a first solvent, wherein the first solvent is a polar solvent capable of dissolving levofloxacin, wherein the polar solvent capable of dissolving levofloxacin is selected from the group consisting of dimethylsulfoxide (DMSO), isobutanol, n-BuOH, ketone, propylene-glycol-monomethyl-ether (PGME) and dimethyl acetamide (DMA);
adding water or a polar solvent comprising water to precipitate levofloxacin, wherein the polar solvent is selected from the group consisting of isopropyl alcohol (IPA), IPA/H₂O, BuOH, acetonitrile (ACN), methyl ethyl ketone (MEK), and DMSO/H₂O; and recovering the (S)-(−)-9,10-difluoro-3-methyl-7-oxo-2,3-dihydro-7H-pyrido[1,2,3-de][1,4]benzoxazine-6-carboxylic acid hemihydrate.

7. A method of converting a levofloxacin form to (S)-(−)-9,10-difluoro-3-methyl-7-oxo-2,3-dihydro-7H-pyrido[1,2,3-de][1,4]benzoxazine-6-carboxylic acid hemihydrate comprising:

storing one or more forms selected from the group consisting of Forms A, B, C, F, G and H for a sufficient time to permit the one or more forms to convert to (S)-(−)-9,10-difluoro-3-methyl-7-oxo-2,3-dihydro-7H-pyrido[1,2,3-de][1,4]benzoxazine-6-carboxylic acid hemihydrate.

8. A method of converting a levofloxacin form to (S)-(−)-9,10-difluoro-3-methyl-7-oxo-2,3-dihydro-7H-pyrido[1,2,3-de][1,4]benzoxazine-6-carboxylic acid hemihydrate comprising:

providing one or more forms selected from the group consisting of Forms A, B, C, F, G and H; and
converting the one or more forms to (S)-(−)-9,10-difluoro-3-methyl-7-oxo-2,3-dihydro-7H-pyrido[1,2,3-de][1,4]benzoxazine-6-carboxylic acid hemihydrate.

9. The method of claim 8, wherein the converting step comprises storing the one or more forms.

10. The method of claim 8, wherein the converting step comprises drying the one or more forms.

11. The method of claim 8, wherein the converting step comprises slurrying the one or more forms.

12. A method for preparing (S)-(−)-9,10-difluoro-3-methyl-7-oxo-2,3-dihydro-7H-pyrido[1,2,3-de][1,4]benzoxazine-6-carboxylic acid hemihydrate, comprising:

maintaining levofloxacin at a first elevated temperature in a first solvent, wherein the first solvent is a polar solvent capable of dissolving levofloxacin, wherein the polar solvent capable of dissolving levofloxacin is selected from the group consisting of dimethylsulfoxide (DMSO), alcohol, ketone, propylene-glycol-monomethyl-ether (PGME) and dimethyl acetamide (DMA);

adding water or a polar solvent comprising water to precipitate levofloxacin, wherein the polar solvent is selected from the group consisting of isopropyl alcohol (IPA), IPA/H₂O, BuOH, acetonitrile (ACN), methyl ethyl ketone (MEK), and DMSO/H₂O; and recovering (S)-(−)-9,10-difluoro-3-methyl-7-oxo-2,3-dihydro-7H-pyrido[1,2,3-de][1,4]benzoxazine-6-carboxylic acid hemihydrate, further comprising slurrying the precipitate of levofloxacin in acetonitrile after the adding step and before the recovery step.

13. A method for preparing (S)-(−)-9,10-difluoro-3-methyl-7-oxo-2,3-dihydro-7H-pyrido[1,2,3-de][1,4]benzoxazine-6-carboxylic acid hemihydrate, comprising slurrying a solvate of levofloxacin in acetonitrile to form (S)-(−)-9-fluoro-2,3-dihydro-3-methyl-10-(4-methyl-1-piperazinyl)-7-oxo-7H-pyrido[1,2,3-de]-1,4-benzoxazine-6-carboxylic acid hemihydrate.

14. The method of claim 13, wherein the solvate is levofloxacin Form G.

15. The method of claim 13, wherein the solvate is levofloxacin Form H.

16. A method for preparing (S)-(−)-9,10-difluoro-3-methyl-7-oxo-2,3-dihydro-7H-pyrido[1,2,3-de][1,4]benzoxazine-6-carboxylic acid hemihydrate comprising storing a levofloxacin solvate for an amount of time sufficient for the levofloxacin solvate to convert to the (S)-(−)-9,10-difluoro-3-methyl-7-oxo-2,3-dihydro-7H-pyrido[1,2,3-de][1,4]benzoxazine-6-carboxylic acid hemihydrate by absorbing atmospheric water.

17. A method for preparing (S)-(−)-9,10-difluoro-3-methyl-7-oxo-2,3-dihydro-7H-pyrido[1,2,3-de][1,4]benzoxazine-6-carboxylic acid hemihydrate comprising
(a) mixing crude levofloxacin with DMSO to form a mixture;
(b) heating the mixture to until complete dissolution;
(c) adding water;
(d) cooling the product of step (c) to room temperature to form a precipitate; and
(e) filtering the product of step (d) to recover the precipitate as the (S)-(−)-9,10-difluoro-3-methyl-7-oxo-2,3-dihydro-7H-pyrido[1,2,3-de][1,4]benzoxazine-6-carboxylic acid hemihydrate.

18. A method for preparing (S)-(−)-9,10-difluoro-3-methyl-7-oxo-2,3-dihydro-7H-pyrido[1,2,3-de][1,4]benzoxazine-6-carboxylic acid hemihydrate comprising
(a) mixing crude levofloxacin with a solvent selected from methyl ethyl ketone, n-butanol and acetonitrile to form a suspension;
(b) heating the suspension to reflux until complete dissolution;
(c) cooling the product of step (b) to form a precipitate; and
(d) filtering the product of step (c) to recover the precipitate as the (S)-(−)-9,10-difluoro-3-methyl-7-oxo-2,3-dihydro-7H-pyrido[1,2,3-de][1,4]benzoxazine-6-carboxylic acid hemihydrate.

19. The method of claim 18, wherein the solvent is methyl ethyl ketone or n-butanol.

20. A method for preparing (S)-(−)-9,10-difluoro-3-methyl-7-oxo-2,3-dihydro-7H-pyrido[1,2,3-de][1,4]benzoxazine-6-carboxylic acid hemihydrate, comprising:

maintaining levofloxacin at a first elevated temperature in a first solvent, wherein the first solvent is a polar solvent capable of dissolving levofloxacin, wherein the polar solvent capable of dissolving levofloxacin is selected from the group consisting of dimethylsulfoxide (DMSO), alcohol, ketone, propylene-glycol-monomethyl-ether (PGME) and dimethyl acetamide (DMA);

adding water or a polar solvent comprising water to precipitate levofloxacin, wherein the polar solvent is selected from the group consisting of isopropyl alcohol (IPA), IPA/H₂O, BuOH, acetonitrile (ACN), methyl ethyl ketone (MEK), and DMSO/H₂O; and recovering (S)-(−)-9,10-difluoro-3-methyl-7-oxo-2,3-dihydro-7H-pyrido[1,2,3-de][1,4]benzoxazine-6-carboxylic acid hemihydrate.

21. The method of claim 4, wherein the polar solvent is selected from the group consisting of IPA, IPA/H₂O and ACN.

22. The method of claim 6, wherein the first solvent is selected from the group consisting of dimethyl sulfoxide, isobutanol, propylene-glycol-monomethyl ether and dimethyl acetamide.

23. The method of claim 1, wherein the polar solvent in the adding step is isopropanol or dimethyl sulfoxide.

24. The method of claim 4, wherein the polar solvent in the adding step is isopropanol or dimethyl sulfoxide.

25. The method of claim 6, wherein the polar solvent in the adding step is isopropanol or dimethyl sulfoxide.

26. The method of claim 4, further comprising adding an anti-solvent to the solvent after the reacting step.

27. The method of claim 1, wherein in the maintaining step the mixture of levofloxacin and the polar solvent is stirred or otherwise agitated.

28. The method of claim 1, wherein in the maintaining step the polar solvent is added for a period of about 2 hours.

* * * * *